(12) United States Patent
Wang

(10) Patent No.: US 10,098,979 B1
(45) Date of Patent: Oct. 16, 2018

(54) MICROWAVE AUTO-INDUCTION AROMA DIFFUSER

(71) Applicant: Shenzhen XiaoOu International Technology Co., Ltd., Shenzhen (CN)

(72) Inventor: Xia Wang, Zhumadian (CN)

(*) Notice: Subject to any disclaimer, the term of this patent is extended or adjusted under 35 U.S.C. 154(b) by 0 days.

(21) Appl. No.: 15/819,519

(22) Filed: Nov. 21, 2017

(30) Foreign Application Priority Data

Apr. 17, 2017 (CN) .................. 2017 2 0396993 U

(51) Int. Cl.
*A61L 9/12* (2006.01)
*B05B 17/06* (2006.01)

(52) U.S. Cl.
CPC .......... *A61L 9/122* (2013.01); *B05B 17/0607* (2013.01); *A61L 2209/15* (2013.01)

(58) Field of Classification Search
CPC .. A61L 9/122; A61L 2209/15; B05B 17/0007
See application file for complete search history.

(56) References Cited

U.S. PATENT DOCUMENTS

| | | | |
|---|---|---|---|
| 2006/0175426 A1* | 8/2006 | Schramm | A01M 1/2033 239/69 |
| 2009/0117012 A1* | 5/2009 | Bankers | A01M 1/2038 422/105 |
| 2011/0095044 A1* | 4/2011 | Sipinski | A61L 9/14 222/1 |

* cited by examiner

*Primary Examiner* — Sean E Conley
(74) *Attorney, Agent, or Firm* — Novoclaims Patent Services LLC; Mei Lin Wong

(57) ABSTRACT

A microwave auto-induction aroma diffuser comprises an aroma diffuser body, and the aroma diffuser body consists of a bottom housing, a fan, a DC seat, a DC seat fixed mount, a water tank, a face housing, a water tank spray cover, a main board, an atomizer plate and an atomizer plate bracket. According to the utility model, the aroma diffuser body is provided with a microwave auto-induction switch to realize automatic control over the working state thereof; when people get close, the aroma diffuser starts to work; and when people leave, the aroma diffuser is automatically switched into the standby state.

5 Claims, 1 Drawing Sheet

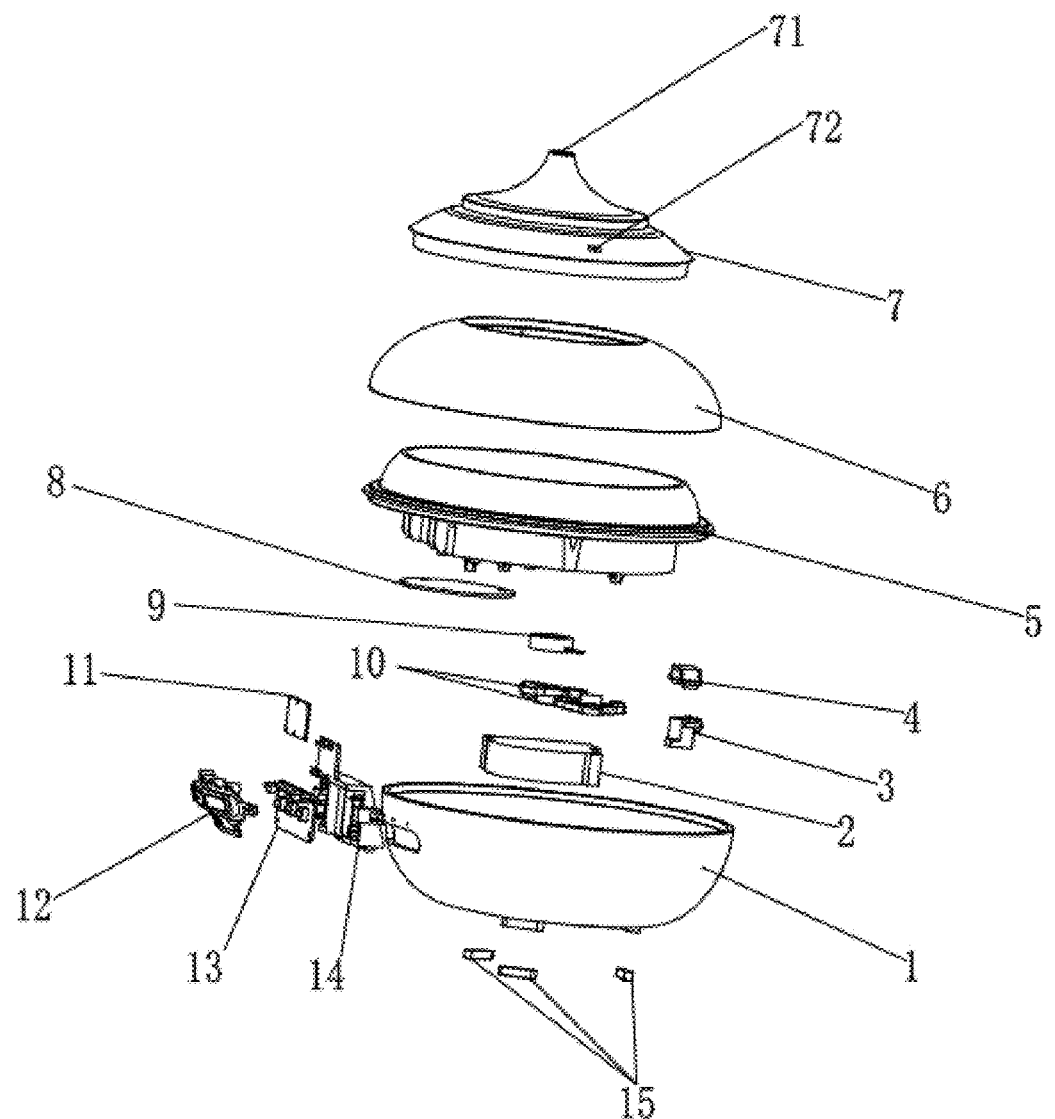

MICROWAVE AUTO-INDUCTION AROMA DIFFUSER

BACKGROUND OF THE INVENTION

Technical Field

The invention relates to the technical field of aroma diffusers, specifically to a microwave auto-induction aroma diffuser.

Description of Related Art

An aroma diffuser utilizes the unique charm of aroma to help communication expand from the visual and audible senses to the sense of smell and then reach a deeper level. In an environment which is optimized with an aroma, customers fully sense the intimate and warm services and this increases the customer's favorable impressions and satisfaction. Aroma diffusers are applicable to various environments such as houses, hotel rooms, lobbies, passages, guest rooms, etc. However, traditional aroma diffusers have an inflexible structure, single function and low intelligence.

BRIEF SUMMARY OF THE INVENTION

The objective of the invention is to provide a microwave auto-induction aroma diffuser to solve the above problems in the prior art.

To fulfill the above objective, the invention employs the following technical solution.

A microwave auto-induction aroma diffuser includes an aroma diffuser body, and the aroma diffuser body consists of a bottom housing, a fan, a power input interface, a water tank, a face housing, a water tank spray cover, a main board, an atomizer plate and an atomizer plate bracket. The atomizer plate is installed on a through-hole at the bottom face of the water tank through the atomizer plate bracket. The water tank is installed at the upper end port in the bottom housing; a fan air inlet is formed at the bottom face of the bottom housing. The fan is installed at the upper end of the fan air inlet. The main board is installed in the bottom housing. The water tank spray cover covers the upper end face of the water tank. The face housing covers the water tank spray cover and is equipped and connected with the bottom housing. The water tank spray cover is formed with a water tank air inlet. The air generated by the fan flows in the space formed by the bottom housing and the face housing, then passes through the water tank air inlet to enter the water tank, and next blows the mist spray generated in the water tank toward a spray nozzle such that the mist spray is jetted out via the spray nozzle. A keypad bracket is arranged on a lateral wall of the bottom housing; the keypad bracket is provided with a keypad; the keypad is provided with keys; and the keypad is also provided with a microwave induction switch.

As a further solution of the invention, the power input interface is a DC seat, and the DC seat is installed on a side through-hole of the bottom housing through a DC seat fixed mount.

As a further solution of the invention, the atomizer plate is an ultrasonic atomizer plate.

As a further solution of the invention, the bottom housing is provided with a non-slip plate at the bottom.

As a further solution of the invention, the water tank spray cover is provided with a spray nozzle.

Compared with the prior art, the invention has the following beneficial effects:

The invention provides a microwave auto-induction aroma diffuser. The invention modifies the traditional aroma diffusers by adding a microwave induction switch on the aroma diffuser so that the aroma diffuser can detect if people are nearby; when people get close, the aroma diffuser starts to work; when people leave, the aroma diffuser is automatically switched into the standby state, thus achieving the effect that the aroma diffuser automatically controls the working state.

BRIEF DESCRIPTION OF THE SEVERAL VIEWS OF THE DRAWINGS

FIG. 1 is a structural view of a microwave auto-induction aroma diffuser.

As shown in the FIGURE, 1—bottom housing; 2—fan; 3—DC seat; 4—DC seat fixed mount; 5—water tank; 6—face housing; 7—water tank spray cover; 71—spray nozzle; 72—water tank air inlet; 8—main board; 9—atomizer plate; 10—atomizer plate bracket; 11—microwave induction switch; 12—key; 13—keypad; 14—keypad bracket; 15—non-slip plate.

DETAILED DESCRIPTION OF THE INVENTION

The technical solution of the invention is described in further detail in conjunction with the embodiment.

Refer to FIG. 1. A microwave auto-induction aroma diffuser includes an aroma diffuser body, and the aroma diffuser body consists of a bottom housing 1, a fan 2, a DC seat 3, a DC seat fixed mount 4, a water tank 5, a face housing 6, a water tank spray cover 7, a main board 8, an ultrasonic atomizer plate 9 and an atomizer plate bracket 10. The DC seat is installed on a side through-hole of the bottom housing through the DC seat fixed mount. The ultrasonic atomizer plate 9 is installed on a through-hole of the bottom face of the water tank 5 through the atomizer plate bracket 10. The water tank 5 is installed at an upper end port in the bottom housing 1. A fan air inlet is formed at the bottom face of the bottom housing 1. The fan 2 is installed at the upper end of the fan air inlet. The main board 8 is installed in the bottom housing 1. The water tank spray cover 7 is installed at the upper end face of the water tank 5 in a covering way. The face housing 6 covers the water tank spray cover 7 and is equipped and connected with the bottom housing 1. The water tank spray cover 7 is formed with a water tank air inlet 72. The air generated by the fan 2 flows in the space formed by the bottom housing 1 and the face housing 6, then passes through the water tank air inlet 72 to enter the water tank 5, and next blows the mist spray generated in the water tank 5 toward a spray nozzle 71 such that the mist spray is jetted out via the spray nozzle 71. A keypad bracket 14 is arranged on a lateral wall of the bottom housing. The keypad bracket 14 is provided with a keypad 13. The keypad is provided with keys 12. The keypad 13 is also provided with a microwave induction switch 11. The bottom housing is provided with a non-slip plate 15 at the bottom. The water tank spray cover 7 is provided with the spray nozzle 71.

The working principle of the invention is as follows. The invention provides a microwave auto-induction aroma diffuser. The invention modifies the traditional aroma diffusers by adding a microwave induction switch on the aroma diffuser so that the aroma diffuser can detect if people are nearby; when people get close, the aroma diffuser starts to work; when people leave, the aroma diffuser is automatically switched into the standby state, thus achieving the effect that the aroma diffuser automatically controls the working state.

The above is a preferable embodiment of the invention, but the invention is not limited to the above embodiment. Those ordinarily skilled in the art can make various modifications within the principle of the invention.

What is claimed is:

1. A microwave auto-induction aroma diffuser, comprising an aroma diffuser body, characterized in that the aroma diffuser body consists of a bottom housing, a fan, a power input interface, a water tank, a face housing, a water tank spray cover, a main board, an atomizer plate and an atomizer plate bracket, wherein the atomizer plate is installed on a through-hole at a bottom face of the water tank through the atomizer plate bracket; the water tank is installed at an upper end port in the bottom housing; a fan air inlet is formed at a bottom face of the bottom housing; the fan is installed at an upper end of the fan air inlet; the main board is installed in the bottom housing; the water tank spray cover covers an upper end face of the water tank; the face housing covers the water tank spray cover and is equipped and connected with the bottom housing; the water tank spray cover is formed with a water tank air inlet; a keypad bracket is arranged on a lateral wall of the bottom housing; the keypad bracket is provided with a keypad; the keypad is provided with keys; and the keypad is also provided with a microwave induction switch.

2. The microwave auto-induction aroma diffuser according to claim 1, characterized in that the power input interface is a DC seat, and the DC seat is installed on a side through-hole of the bottom housing through a DC seat fixed mount.

3. The microwave auto-induction aroma diffuser according to claim 1, characterized in that the atomizer plate is an ultrasonic atomizer plate.

4. The microwave auto-induction aroma diffuser according to claim 1, characterized in that the bottom housing is provided with a non-slip plate at the bottom.

5. The microwave auto-induction aroma diffuser according to claim 1, characterized in that the water tank spray cover is provided with a spray nozzle.

* * * * *